United States Patent
Aqad et al.

(10) Patent No.: US 10,095,109 B1
(45) Date of Patent: Oct. 9, 2018

(54) ACID-CLEAVABLE MONOMER AND POLYMERS INCLUDING THE SAME

(71) Applicant: ROHM AND HAAS ELECTRONIC MATERIALS LLC, Marlborough, MA (US)

(72) Inventors: Emad Aqad, Northborough, MA (US); James W. Thackeray, Braintree, MA (US)

(73) Assignee: ROHM AND HAAS ELECTRONIC MATERIALS LLC, Marlborough, MA (US)

( * ) Notice: Subject to any disclaimer, the term of this patent is extended or adjusted under 35 U.S.C. 154(b) by 0 days.

(21) Appl. No.: 15/475,630

(22) Filed: Mar. 31, 2017

(51) Int. Cl.
| | |
|---|---|
| G03F 7/004 | (2006.01) |
| C07C 69/54 | (2006.01) |
| C08F 220/28 | (2006.01) |
| G03F 7/038 | (2006.01) |
| G03F 7/039 | (2006.01) |
| G03F 7/16 | (2006.01) |
| G03F 7/20 | (2006.01) |
| G03F 7/38 | (2006.01) |
| G03F 7/32 | (2006.01) |

(52) U.S. Cl.
CPC .......... *G03F 7/0045* (2013.01); *C07C 69/54* (2013.01); *C08F 220/28* (2013.01); *G03F 7/038* (2013.01); *G03F 7/039* (2013.01); *G03F 7/162* (2013.01); *G03F 7/168* (2013.01); *G03F 7/20* (2013.01); *G03F 7/327* (2013.01); *G03F 7/38* (2013.01); *C08F 2220/283* (2013.01)

(58) Field of Classification Search
CPC ... G03F 7/004; G03F 7/11; G03F 7/38; G03F 7/40; G03F 7/039; G03F 7/038; C08F 214/16; C08F 114/16
USPC ...................................... 430/270.1
See application file for complete search history.

(56) References Cited

U.S. PATENT DOCUMENTS

| | | | | |
|---|---|---|---|---|
| 8,361,453 B2* | 1/2013 | Uhrich | ............. | A61L 27/18 |
| | | | | 424/78.01 |
| 2010/0248149 A1* | 9/2010 | Tsuchimura | ........ | C08F 224/00 |
| | | | | 430/296 |
| 2014/0080058 A1 | 3/2014 | Cameron et al. | | |
| 2015/0168834 A1* | 6/2015 | Takizawa | ............ | C08F 14/185 |
| | | | | 430/18 |
| 2015/0370170 A1* | 12/2015 | Hirano | ............. | G03F 7/325 |
| | | | | 430/17 |
| 2016/0202608 A1* | 7/2016 | Namai | ............. | G03F 7/0045 |
| | | | | 430/270.1 |

FOREIGN PATENT DOCUMENTS

JP  2015161823 A  9/2015

* cited by examiner

*Primary Examiner* — Amanda C. Walke
(74) *Attorney, Agent, or Firm* — Cantor Colburn LLP

(57) ABSTRACT

A monomer having formula (I):

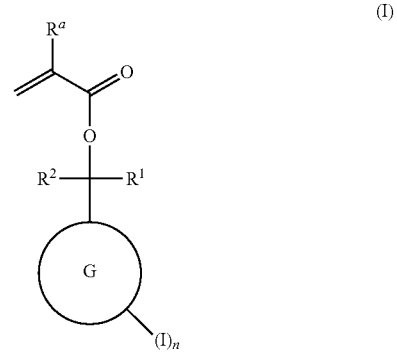

wherein in formula (I), groups and variables are the same as described in the specification.

20 Claims, No Drawings

ACID-CLEAVABLE MONOMER AND POLYMERS INCLUDING THE SAME

FIELD

The present disclosure generally relates to polymer compositions including a photoacid generator. Specifically, the disclosure provides copolymers derived from an iodine-containing monomer.

BACKGROUND

Extreme ultraviolet lithography ("EUVL") is one of the leading technologies options to replace optical lithography for volume semiconductor manufacturing at feature sizes <20 nm. The extremely short wavelength (13.4 nm) is a key enabling factor for high resolution required at multiple technology generations. In addition, the overall system concept—scanning exposure, projection optics, mask format, and resist technology—is quite similar to that used for current optical technologies. Like previous lithography generations, EUVL consists of resist technology, exposure tool technology, and mask technology. The key challenges are EUV source power and throughput. Any improvement in EUV power source will directly impact the currently strict resist sensitivity specification. Indeed, a major issue in EUVL imaging is resist sensitivity, the lower the sensitivity, the greater the source power that is needed or the longer the exposure time that is required to fully expose the resist. The lower the power levels, the more noise affects the line edge roughness (LER) of the printed lines.

Improving EUV sensitivity is a key enabling factor. It has been shown that EUV light absorption cross-section and secondary electron generation yield are critical factors for EUV sensitivity. One way to increase EUV photoresist sensitivity is by increasing its absorption cross-section at 13.5 nm, which is an atomic property of the material that can be theoretically calculated using known atomic absorptions. Typical atoms that make up resist materials, such as carbon, oxygen, hydrogen, and nitrogen possess very weak absorption at 13.5 nm. A fluorine atom has slightly higher absorption and has been used in the search for high EUV absorbing photoresist.

Iodine has remarkably high absorption cross-section at EUV radiation. Recent patent application JP 2015-161823 discloses iodine-containing monomers and corresponding polymers useful for lithographic processing. However, none of these monomers could be readily cleaved by acid. Thus, there remains a need in new iodine-containing high absorbing monomers to produce iodine-containing polymer which can be useful for lithographic processing.

SUMMARY

An embodiment provides a monomer having formula (I):

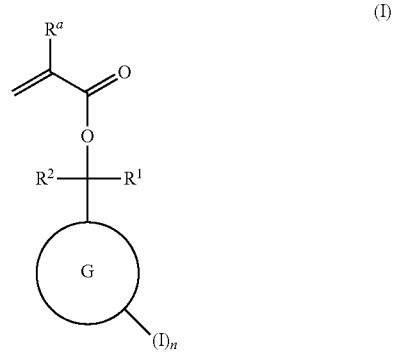

(I)

wherein in formula (I):
$R^a$ is H, F, —CN, $C_{1-10}$ alkyl group, or $C_{1-10}$ fluoroalkyl group;
$R^1$ and $R^2$ are each independently an unsubstituted or substituted $C_{1-10}$ linear or branched alkyl group, an unsubstituted or substituted $C_{3-10}$ cycloalkyl group, an unsubstituted or substituted $C_{3-10}$ alkenylalkyl group, an unsubstituted or substituted $C_{3-10}$ alkynylalkyl group, or an unsubstituted or substituted $C_{6-30}$ aryl group, wherein $R^1$ and $R^2$ optionally include at least one linking group selected from O and S, and wherein $R^1$ and $R^2$ together optionally form a ring;

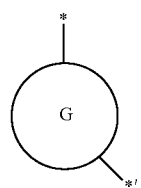

represents a monocyclic or polycyclic unsubstituted or substituted $C_{6-30}$ arylene group or a monocyclic or polycyclic unsubstituted or substituted $C_{3-30}$ heteroarylene group, wherein "*" and "*'" indicate a point of attachment to a neighboring group or atom,
"I" represents iodine, and
n is 1, 2, 3, 4, 5, 6, 7, 8, and 9.

Another embodiment provides a copolymer including a polymerized product of the monomer having formula (I) and at least one unsaturated monomer which is different from the monomer having formula (I).

Yet another embodiment provides a copolymer including a polymerized product of a photoacid generator monomer including a polymerizable group and the monomer having formula (I).

DETAILED DESCRIPTION

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third, etc., may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, when a definition is not otherwise provided, the term "alkyl group" refers to a group derived from a straight or branched chain saturated aliphatic hydrocarbon having the specified number of carbon atoms and having a valence of at least one.

As used herein, when a definition is not otherwise provided, the term "fluoroalkyl group" refers to an alkyl group in which one or more hydrogen atoms are replaced with fluorine atoms.

As used herein, when a definition is not otherwise provided, the term "alkoxy group" refers to "alkyl-O—", wherein the term "alkyl" has the same meaning as described above.

As used herein, when a definition is not otherwise provided, the term "fluoroalkoxy group" refers to an alkoxy group in which one or more hydrogen atoms are replaced with fluorine atoms.

As used herein, when a definition is not otherwise provided, the term "cycloalkyl group" refers to a monovalent group having one or more saturated rings in which all ring members are carbon.

As used herein, when a definition is not otherwise provided, the term "alkenyl group" refers to a straight or branched chain, monovalent hydrocarbon group having at least one carbon-carbon double bond.

As used herein, when a definition is not otherwise provided, the term "alkenylalkyl group" refers to "alkenyl-alkyl-", wherein the terms "alkenyl" and "alkyl" have the same meaning as described above.

As used herein, when a definition is not otherwise provided, the term "alkynyl group" refers to a straight or branched chain, monovalent hydrocarbon group having at least one carbon-carbon triple bond.

As used herein, when a definition is not otherwise provided, the term "alkynylalkyl group" refers to "alkynyl-alkyl-", wherein the terms "alkynyl" and "alkyl" have the same meaning as described above.

As used herein, when a definition is not otherwise provided, the term "aryl", which is used alone or in combination, refers to an aromatic or heteroaromatic hydrocarbon containing at least one ring and having the specified number of carbon atoms. The term "aryl" may be construed as including a group with an aromatic or heteroaromatic ring fused to at least one cycloalkyl or heterocycloalkyl ring. The "aryl" group may include one or more heteroatom(s) independently selected from nitrogen (N), oxygen (O), P (phosphorus), and sulfur (S).

As used herein, when a definition is not otherwise provided, the term "aryloxy group" refers to "aryl-O—", wherein the term "aryl" has the same meaning as described above.

As used herein, when a definition is not otherwise provided, the term "aralkyl group" refers to a substituted or unsubstituted aryl group covalently linked to an alkyl group that is linked to a compound.

As used herein, when a definition is not otherwise provided, the term "alkylene group" refers to a straight or branched saturated aliphatic hydrocarbon group having a valence of at least two, optionally substituted with one or more substituents where indicated, provided that the valence of the alkylene group is not exceeded.

As used herein, when a definition is not otherwise provided, the term "cycloalkylene group" refers to a cyclic hydrocarbon group having a valence of at least two, optionally substituted with one or more substituents where indicated, provided that the valence of the cycloalkylene group is not exceeded.

As used herein, when a definition is not otherwise provided, the term "arylene group" refers to a functional group having a valence of at least two obtained by removal of two hydrogens in an aromatic ring, optionally substituted with one or more substituents where indicated, provided that the valence of the arylene group is not exceeded.

As used herein, when a definition is not otherwise provided, the term "aralkylene group" refers to a functional group having a valence of at least two obtained by removal of two hydrogens from the alkyl-substituted aromatic compound, optionally substituted with one or more substituents where indicated, provided that the valence of the aralkylene group is not exceeded.

As used herein, when a definition is not otherwise provided, the term "heteroarylene group" refers to a functional group having a valence of at least two obtained by removal of two hydrogens in a heteroaromatic ring, optionally substituted with one or more substituents where indicated, provided that the valence of the heteroarylene group is not exceeded.

An embodiment of the present disclosure provides a monomer having formula (I):

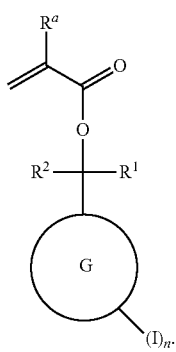

(I)

In formula (I), $R^a$ may be H, F, —CN, $C_{1-10}$ alkyl group, or $C_{1-10}$ fluoroalkyl group;

$R^1$ and $R^2$ may be each independently an unsubstituted or substituted $C_{1-10}$ linear or branched alkyl group, an unsubstituted or substituted $C_{3-10}$ cycloalkyl group, an unsubstituted or substituted $C_{3-10}$ alkenylalkyl group, an unsubstituted or substituted $C_{3-10}$ alkynylalkyl group, or an unsubstituted or substituted $C_{6-30}$ aryl group, wherein $R^1$ and $R^2$ optionally include at least one linking group selected from O and S, and wherein $R^1$ and $R^2$ may together optionally form a ring;

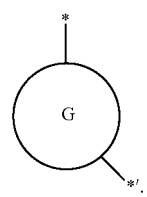

may represent a monocyclic or polycyclic unsubstituted or substituted $C_{6-30}$ arylene group or a monocyclic or polycyclic unsubstituted or substituted $C_{3-30}$ heteroarylene group, wherein "*" and "*'" indicate a point of attachment to a neighboring group or atom, "I" represents iodine, and n may be 1, 2, 3, 4, 5, 6, 7, 8, and 9.

In the above monomer, the $C_{6-30}$ arylene group may be a monocyclic $C_{6-30}$ arylene group, a fused bicyclic $C_{6-30}$ arylene group, or a singly bonded $C_{6-30}$ arylene group. The $C_{6-30}$ arylene group may be a 1,2-phenylene group, a 1,3-phenylene group, and a 1,4-phenylene group. The fused bicyclic $C_{6-30}$ arylene group may be a disubstituted naphthalene group, a disubstituted anthracene group, or a disubstituted phenanthrene group. The singly bonded $C_{6-30}$ arylene group may be a disubstituted biphenylene group or a disubstituted terphenylene group. The $C_{3-30}$ heteroarylene group may be a monocyclic $C_{3-30}$ heteroarylene group, a fused bicyclic $C_{3-30}$ heteroarylene group, or a singly bonded $C_{3-30}$ heteroarylene group.

In an embodiment, each of $R^1$ and $R^2$ may be an unsubstituted or substituted $C_{1-10}$ linear or branched alkyl groups. For example, both $R^1$ and $R^2$ may be an unsubstituted or substituted linear $C_{1-10}$ alkyl group, one of $R^1$ and $R^2$ may be an unsubstituted or substituted linear $C_{1-10}$ alkyl group and the other one of $R^1$ and $R^2$ may be an unsubstituted or substituted branched $C_{1-10}$ alkyl group, or both $R^1$ and $R^2$ may be an unsubstituted or substituted branched $C_{1-10}$ alkyl group. In an example, one of $R^1$ and $R^2$ may be an unsubstituted $C_{1-10}$ linear or branched alkyl group and the other one of $R^1$ and $R^2$ may be a $C_{1-10}$ linear or branched alkyl group substituted with at least one fluorine atom.

Each of $R^1$ and $R^2$ may include a linking group selected from O and S. The linking group may be present either inside of $R^1$ and $R^2$ or at the site of their connection to a neighboring group. Examples of groups $R^1$ and $R^2$ when the linking group is present inside are $CH_3OCH_2$—, $CH_3OCH_2CH_2$—, $CH_3CH_2OCH_2$—. Examples of $R^1$ and $R^2$ when the linking group is present at the site of their connection are $CH_3O$—, $CH_3CH_2O$—, and $CH_3CH_2CH_2O$—.

In an embodiment, groups $R^1$ and $R^2$ may together optionally form a ring. For example, when $R^1$ is methyl and $R^2$ is n-propyl, $R^1$ and $R^2$ may form a cyclopentane ring. In another example, when $R^1$ is ethyl and $R^2$ is n-propyl, $R^1$ and $R^2$ may form a cyclohexane ring.

In formula (I), the variable n represents a number of iodine atoms attached to the divalent group

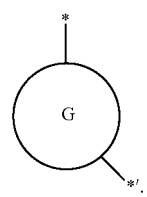

The number of iodine atoms n may vary depending on the nature of this group and may be 1, 2, 3, 4, 5, 6, 7, 8, or 9. For example, n may be 1, 2, or 3.

Specific examples of the monomer having formula (I) may be represented by the following chemical formulae:

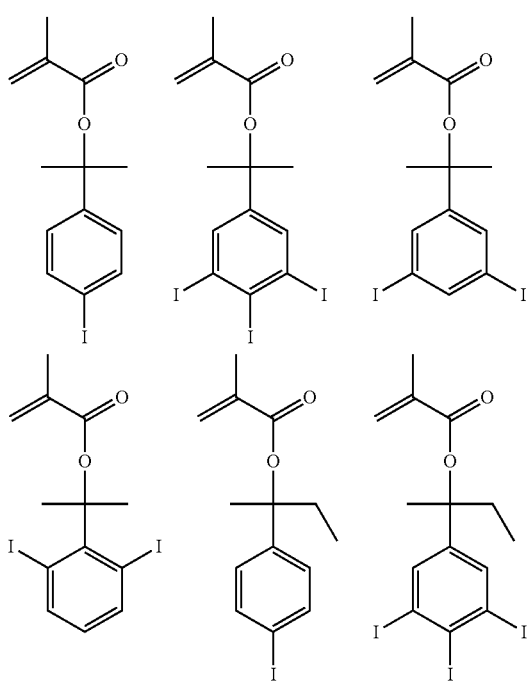

-continued

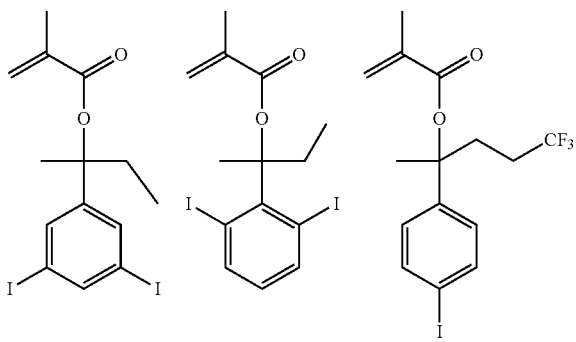

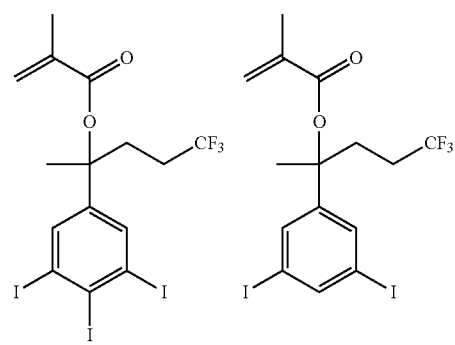

Another embodiment provides a copolymer including a polymerized product of the monomer having formula (I) and at least one unsaturated monomer which is different from the monomer having formula (I):

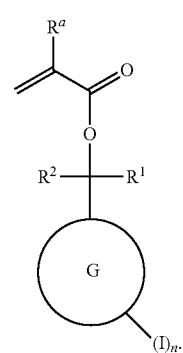

In formula (I), $R^a$, $R^1$, $R^2$,

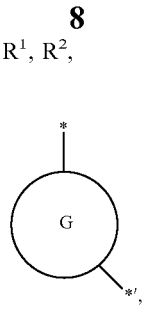

"I", and n are the same as described above.

The unsaturated monomer which is different from the monomer having formula (I) may be a base-soluble monomer, a lactone-containing monomer, or a combination thereof.

For example, the unsaturated monomer may be a base-soluble monomer of formula (II):

In formula (II), $Q_1$ may be an ester-containing or non-ester containing group selected from $C_{1-20}$ alkyl, $C_{3-20}$ cycloalkyl, $C_{6-20}$ aryl, and $C_{7-20}$ aralkyl group. In an embodiment, where an ester is included, the ester may form a connective link between $Q_1$ and the point of attachment to the double bond. In this way, where $Q_1$ is an ester group, formula (II) may be a (meth)acrylate monomer. In another embodiment, where an ester is not included, $Q_1$ may be aromatic, so that formula (II) may be, for example, a styrenic monomer or vinyl naphthoic monomer. $Q_1$ may be fluorinated or non-fluorinated. Further in formula (II), a may be an integer of 1 to 3, for example, a may be 1 or 2.

Also in formula (II), W may be a base-reactive group including —C(=O)—OH; —C(CF$_3$)$_2$OH; —NH—SO$_2$—Y$^1$ where Y$^1$ is F or $C_{1-4}$ perfluoroalkyl; an aromatic —OH; or an adduct of any of the foregoing with a vinyl ether. In an embodiment, where Q is non-aromatic (e.g., where formula (II) includes a (meth)acrylate structure having an ester linked alkyl or cycloalkyl group Q), W may be —C(CF$_3$)$_2$OH. In another embodiment, where Q is aromatic (e.g., where Q is either ester-linked or non-ester linked and is an aromatic group such as phenyl or naphthyl), W may be OH or —C(CF$_3$)$_2$OH. It is contemplated that any of the base-reactive groups may further be protected by an acid decomposable acetal leaving group (e.g., having a generic structure —O—CH(R')—O—R" where R' may be a methyl, ethyl, or other alkyl group) Such groups are adducts of a vinyl ether, such as, for example, ethyl vinyl ether, propyl vinyl ether, t-butyl vinyl ether, cyclohexylvinyl ether, the 2-vinyloxyethyl ester of 1-adamantane carboxylic acid, 2-naphthoyl ethyl vinyl ether, or other such vinyl ethers.

W may be a base reactive group including a fluorinated ester of the form —C(=O)—OCF$_2$R or —OC(=O)CF$_2$R, wherein R is a $C_{1-10}$ alkyl group or a $C_{1-10}$ fluoroalkyl group.

Exemplary base-soluble monomers having formula (II) may include:

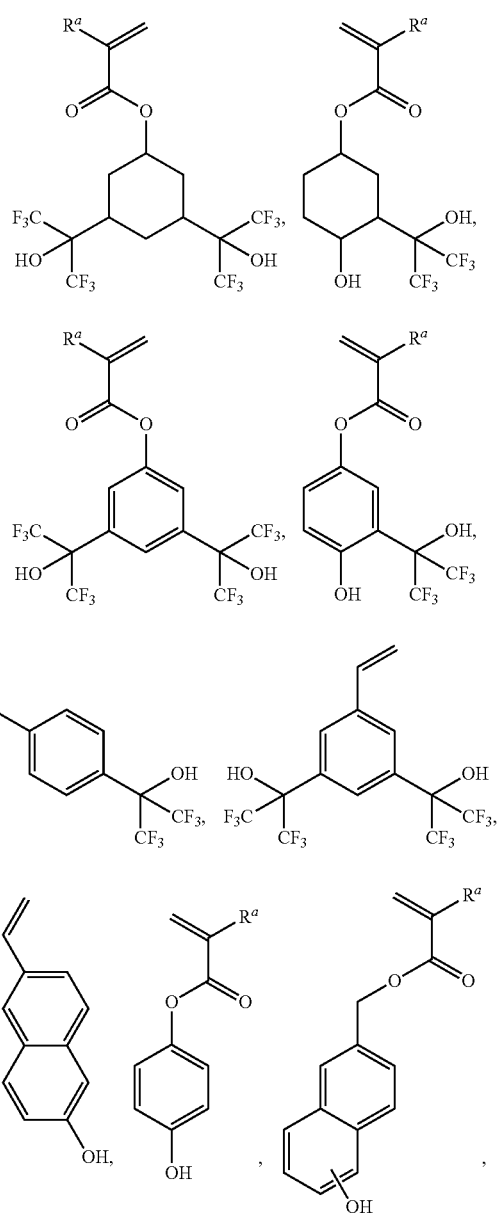

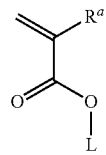

or a combination including at least one of the foregoing, wherein $R^a$ is H, F, $C_{1-6}$ alkyl, or $C_{1-6}$ fluoroalkyl.

The unsaturated monomer may also be a lactone-containing monomer of formula (III):

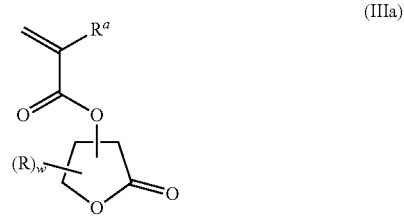

(III)

In formula (III), L may be a monocyclic, polycyclic, or fused polycyclic $C_{4-20}$ lactone-containing group. Such lactone groups may be included to improve both adhesion of the polymer to a substrate, and to moderate the dissolution of the polymer in a base developer. In an embodiment, L may be a monocyclic $C_{4-6}$ lactone which is attached to a (meth)acrylate moiety through a monocycle ring carbon; or L may be a $C_{6-10}$ fused polycyclic lactone based on a norbornane-type structure.

In an embodiment, a lactone-containing monomer may have formula (IIIa):

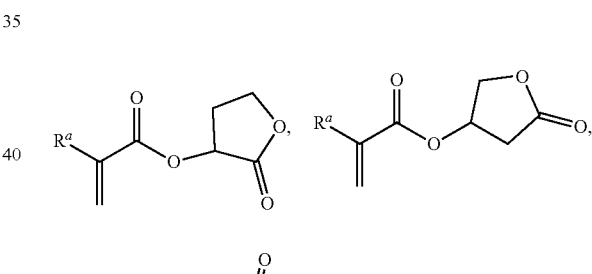

(IIIa)

wherein $R^a$ is H, F, $C_{1-6}$ alkyl, or $C_{1-6}$ fluoroalkyl, R is a $C_{1-10}$ alkyl, cycloalkyl, or heterocycloalkyl, and w is an integer of 0 to 6.

It will be appreciated in formula (IIIa) that R may be separate or may be attached to the lactone ring and/or one or more R groups, and that the methacrylate moiety may be attached to the lactone ring directly, or indirectly through R.

Exemplary lactone-containing monomers of formulae (III) and (IIIa) may include:

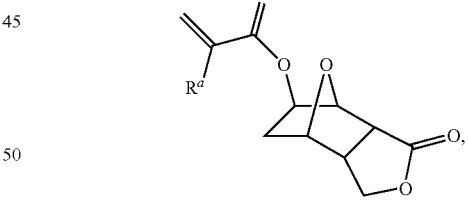

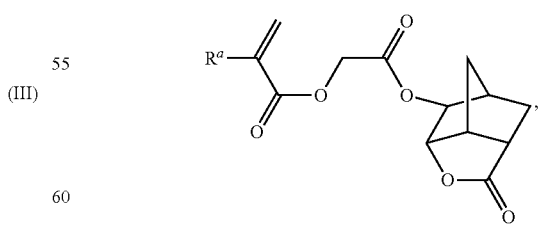

or a combination including at least one of the foregoing, wherein $R^a$ is H, F, $C_{1-6}$ alkyl, or $C_{1-6}$ fluoroalkyl.

In an embodiment, the copolymer may include a polymerized product having the following structure:

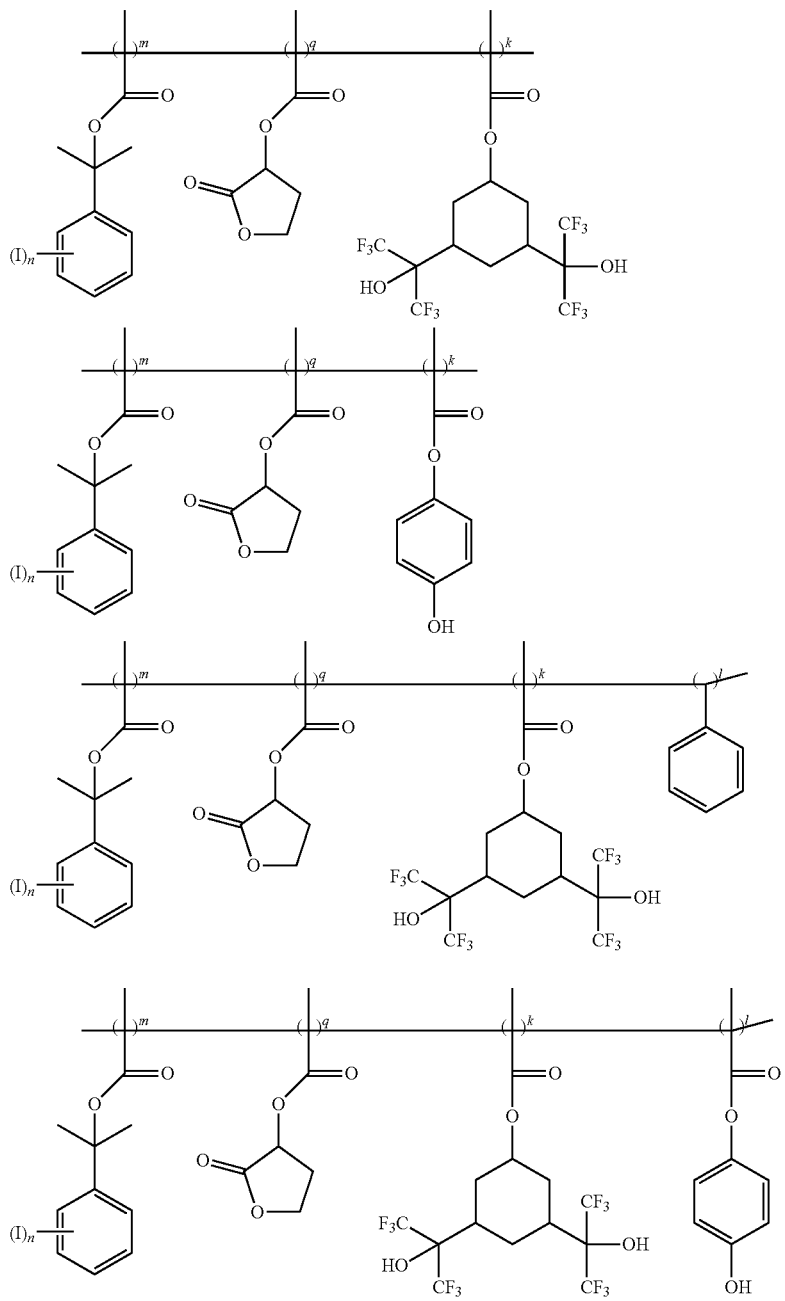

wherein k, l, m, and q represent mole fractions of the corresponding repeating units, and "I" is iodine and variable n is the same as described above.

Another embodiment further provides a photoresist composition including the above copolymer and a non-polymerizable photoacid generator monomer having formula $G^+A^-$, wherein $A^-$ is a non-polymerizable organic anion and $G^+$ has formula (IV):

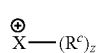

(IV)

In formula (IV),

X may be S or I, each $R^c$ may be halogenated or non-halogenated, and is independently a $C_{1-30}$ alkyl group; a polycyclic or monocyclic $C_{3-30}$ cycloalkyl group; a polycyclic or monocyclic $C_{4-30}$ aryl group, wherein when X is S, one of the $R^c$ groups is optionally attached to one adjacent $R^c$ group by a single bond, and z is 2 or 3, and wherein when X is I, z is 2, or when X is S, z is 3.

For example, cation $G^+$ may have formula (V), (VI), or (VII):

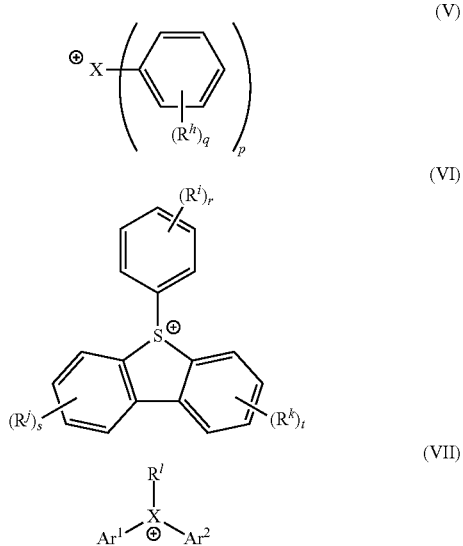

wherein

X is I or S, $R^h$, $R^i$, $R^j$, and $R^k$ are unsubstituted or substituted and are each independently hydroxy, nitrile, halogen, $C_{1-30}$ alkyl, $C_{1-30}$ fluoroalkyl, $C_{3-30}$ cycloalkyl, $C_{1-30}$ fluorocycloalkyl, $C_{1-30}$ alkoxy, $C_{3-30}$ alkoxycarbonylalkyl, $C_{3-30}$ alkoxycarbonylalkoxy, $C_{3-30}$ cycloalkoxy, $C_{5-30}$ cycloalkoxycarbonylalkyl, $C_{5-30}$ cycloalkoxycarbonylalkoxy, $C_{1-30}$ fluoroalkoxy, $C_{3-30}$ fluoroalkoxycarbonylalkyl, $C_{3-30}$ fluoroalkoxycarbonylalkoxy, $C_{3-30}$ fluorocycloalkoxy, $C_{5-30}$ fluorocycloalkoxycarbonylalkyl, $C_{5-30}$ fluorocycloalkoxycarbonylalkoxy, $C_{6-30}$ aryl, $C_{6-30}$ fluoroaryl, $C_{6-30}$ aryloxy, or $C_{6-30}$ fluoroaryloxy, each of which is unsubstituted or substituted;

$Ar^1$ and $Ar^2$ are independently $C_{10-30}$ fused or singly bonded polycyclic aryl groups;

$R^1$ is a lone pair of electrons where X is I, or a $C_{6-20}$ aryl group where X is S;

p is an integer of 2 or 3, wherein when X is I, p is 2, and where X is S, p is 3, q and r are each independently an integer from 0 to 5, and s and t are each independently an integer from 0 to 4.

In formulae (V), (VI), or (VII), at least one of $R^h$, $R^i$, $R^j$, and $R^k$ may be an acid-cleavable group. In an embodiment, the acid-cleavable group may be (i) a tertiary $C_{1-30}$ alkoxy (for example, a tert-butoxy group), a tertiary $C_{3-30}$ cycloalkoxy group, a tertiary $C_{1-30}$ fluoroalkoxy group, (ii) a tertiary $C_{3-30}$ alkoxycarbonylalkyl group, a tertiary $C_{5-30}$ cycloalkoxycarbonylalkyl group, a tertiary $C_{3-30}$ fluoroalkoxycarbonylalkyl group, (iii) a tertiary $C_{3-30}$ alkoxycarbonylalkoxy group, a tertiary $C_{5-30}$ cycloalkoxycarbonylalkoxy group, a tertiary $C_{3-30}$ fluoroalkoxycarbonylalkoxy group, or (iv) a $C_{2-30}$ acetal group including moiety —O—C($R^{11}R^{12}$)—O— (wherein $R^{11}R^{12}$ are each independently hydrogen or a $C_{1-30}$ alkyl group).

The photoresist composition including the copolymer and the non-polymerizable photoacid generator monomer as disclosed herein may be used to provide a layer including the photoresist. A coated substrate may be formed from the photoresist composition. Such a coated substrate includes: (a) a substrate having one or more layers to be patterned on a surface thereof; and (b) a layer of the photoresist composition over the one or more layers to be patterned.

Substrates may be any dimension and shape, and are preferably those useful for photolithography, such as silicon, silicon dioxide, silicon-on-insulator (SOI), strained silicon, gallium arsenide, coated substrates including those coated with silicon nitride, silicon oxynitride, titanium nitride, tantalum nitride, ultrathin gate oxides such as hafnium oxide, metal or metal coated substrates including those coated with titanium, tantalum, copper, aluminum, tungsten, alloys thereof, and combinations thereof. Preferably, the surfaces of substrates herein include critical dimension layers to be patterned including, for example, one or more gate-level layers or other critical dimension layers on the substrates for semiconductor manufacture. Such substrates may preferably include silicon, SOI, strained silicon, and other such substrate materials, formed as circular wafers having dimensions such as, for example, 20 cm, 30 cm, or larger in diameter, or other dimensions useful for wafer fabrication production.

Further, a method of forming an electronic device includes (a) applying (casting) a layer of the above photoresist composition on a surface of the substrate; (b) pattern-wise exposing the photoresist composition layer to activating radiation; and (c) developing the exposed photoresist composition layer to provide a resist relief image.

Applying may be accomplished by any suitable method, including spin coating, spray coating, dip coating, doctor blading, or the like. Applying the layer of photoresist is preferably accomplished by spin-coating the photoresist in solvent using a coating track, in which the photoresist is dispensed on a spinning wafer. During dispensing, the wafer may be spun at a speed of up to 4,000 rpm, preferably from about 200 to 3,000 rpm, and more preferably 1,000 to 2,500 rpm. The coated wafer is spun to remove solvent, and baked on a hot plate to remove residual solvent and free volume from the film to make it uniformly dense.

The casting solvent can be any suitable solvent known to one of ordinary skill in the art. For example, the casting solvent can be an aliphatic hydrocarbon (such as hexane, heptane, and the like), an aromatic hydrocarbon (such as toluene, xylene, and the like), a halogenated hydrocarbon (such as dichloromethane, 1,2-dichloroethane, 1-chlorohexane, and the like), an alcohol (such as methanol, ethanol, 1-propanol, iso-propanol, tert-butanol, 2-methyl-2-butanol, 4-methyl-2-pentanol, and the like), water, an ether (such as diethyl ether, tetrahydrofuran, 1,4-dioxane, anisole, and the like), a ketone (such as acetone, methyl ethyl ketone, methyl isobutyl ketone, 2-heptanone, cyclohexanone, and the like), an ester (such as ethyl acetate, n-butyl acetate, propylene glycol monomethyl ether acetate ("PGMEA"), ethyl lactate, ethyl acetoacetate, and the like), a lactone (such as γ-butyrolactone, ε-caprolactone, and the like), a nitrile (such as acetonitrile, propionitrile, and the like), an aprotic bipolar solvent (such as dimethylsulfoxide, dimethylformamide, and the like), or a combination thereof. The choice of the casting solvent depends on a particular photoresist composition and can be readily made by one of ordinary skill in the art based on knowledge and experience.

Pattern-wise exposure is then carried out using an exposure tool such as a stepper, in which the film is irradiated through a pattern mask and thereby is exposed pattern-wise. The method preferably uses advanced exposure tools generating activating radiation at wavelengths capable of high resolution including extreme-ultraviolet ("EUV") or e-beam radiation. It will be appreciated that exposure using activating radiation decomposes the PAG in the exposed areas and generates acid and decomposition by-products, and that the acid or the by-products then effectuates a chemical change in the polymer and nanoparticles (deblocking the acid sensitive group to generate a base-soluble group, or alternatively, catalyzing a crosslinking reaction in the exposed areas). The resolution of such exposure tools may be less than 30 nm.

Developing the exposed photoresist layer is then accomplished by treating the exposed layer to a suitable developer capable of selectively removing the exposed portions of the film (where the photoresist is a positive tone) or removing the unexposed portions of the film (where the photoresist is crosslinkable in the exposed regions, i.e., a negative tone). Preferably, the photoresist is a negative tone, based on a polymer having pendant and/or free acid groups or by-products (derived from bound or free PAG following irradiation) that inhibit the dissolution of the nanoparticles, and the developer is preferably solvent based. A pattern forms by developing. The solvent developer can be any suitable developer known in the art. For example, the solvent developer can be an aliphatic hydrocarbon (such as hexane, heptane, and the like), an aromatic hydrocarbon (such as toluene, xylene, and the like), a halogenated hydrocarbon (such as dichloromethane, 1,2-dichloroethane, 1-chlorohexane, and the like), an alcohol (such as methanol, ethanol, 1-propanol, iso-propanol, tert-butanol, 2-methyl-2-butanol, 4-methyl-2-pentanol, and the like), water, an ether (such as diethyl ether, tetrahydrofuran, 1,4-dioxane, anisole, and the like), a ketone (such as acetone, methyl ethyl ketone, methyl isobutyl ketone, 2-heptanone, cyclohexanone, and the like), an ester (such as ethyl acetate, n-butyl acetate, propylene glycol monomethyl ether acetate ("PGMEA"), ethyl lactate, ethyl acetoacetate, and the like), a lactone (such as γ-butyrolactone, ε-caprolactone, and the like), a nitrile (such as acetonitrile, propionitrile, and the like), an aprotic bipolar solvent (such as dimethylsulfoxide, dimethylformamide, and the like), or a combination thereof. In an embodiment, the solvent developer may be a miscible mixture of solvents, for example, a mixture of an alcohol (iso-propanol) and ketone (acetone). The choice of the developer solvent depends on a particular photoresist composition and can be readily made by one of ordinary skill in the art based on knowledge and experience.

The photoresist may, when used in one or more such pattern-forming processes, be used to fabricate electronic and optoelectronic devices such as memory devices, processor chips (CPUs), graphics chips, and other such devices.

Yet another embodiment provides a copolymer including a polymerized product of a photoacid generator monomer including a polymerizable group and the monomer having formula (I):

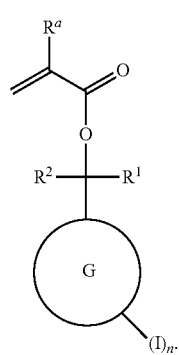

(I)

In formula (I), $R^a$, $R^1$, $R^2$,

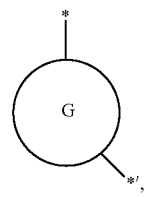

"l", and n are the same as described above.

The photoacid generator monomer including a polymerizable group may be represented by formula (VIII):

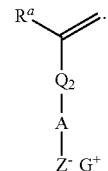

(VIII)

In formula (VIII), each $R^a$ may independently be H, F, $C_{1-10}$ alkyl, or $C_{1-10}$ fluoroalkyl. As used throughout this specification, "fluoro" or "fluorinated" means that one or more fluorine groups are attached to the associated group. For example, by this definition and unless otherwise specified, "fluoroalkyl" encompasses monofluoroalkyl, difluoroalkyl, etc., as well as perfluoroalkyl in which substantially all carbon atoms of the alkyl group are substituted with fluorine atoms; similarly, "fluoroaryl" means monofluoroaryl, perfluoroaryl, etc. "Substantially all" in this context means greater than or equal to 90%, preferably greater than or equal to 95%, and still more preferably greater than or equal to 98% of all atoms attached to carbon are fluorine atoms.

In formula (VIII), $Q_2$ is a single bond or an ester-containing or non-ester containing, fluorinated or non-fluorinated group selected from $C_{1-20}$ alkyl, $C_{3-20}$ cycloalkyl, $C_{6-20}$ aryl, and $C_{7-20}$ aralkyl. For example, where an ester is included, the ester forms a connective link between $Q_2$ and the point of attachment to the double bond. In this way, where $Q_2$ is an ester group, formula (VIII) may be a (meth)acrylate monomer. Where an ester is not included, $Q_2$ may be aromatic, so that formula (VIII) may be, for example, a styrenic monomer or vinyl naphthoic monomer.

Also, in formula (VIII), A is an ester-containing or non ester-containing, fluorinated or non-fluorinated group selected from $C_{1-20}$ alkyl, $C_{3-20}$ cycloalkyl, $C_{6-20}$ aryl, or $C_{7-20}$ aralkyl. Useful A groups may include fluorinated aromatic moieties, straight chain fluoroalkyl, or branched fluoroalkyl esters. For example, A may be a $-[(C(R^e)_2)_x(=O)O]_c-(C(R^f)_2)_y(CF_2)_z-$ group, or an o-, m- or p-substituted $-C_6R^g_4-$ group, where each $R^e$, $R^f$, and $R^g$ are each independently H, F, $C_{1-6}$ fluoroalkyl, or $C_{1-6}$ alkyl, c is 0 or 1, x is an integer of 1 to 10, y and z are independently integers of from 0 to 10, and the sum of y+z is at least 1.

Also, in formula (VIII), $Z^-$ is an anionic group including a sulfonate ($-SO_3-$), the anion of a sulfonamide ($-SO_2(N^-)R'$ where R' is a $C_{1-10}$ alkyl or $C_{6-20}$ aryl, or the anion of a sulfonimide. Where $Z^-$ is a sulfonimide, the sulfonimide may be an asymmetric sulfonimide having the general structure $A-SO_2-(N^-)-SO_2-Y^2$, where A is as described above, and $Y^2$ is a straight chain or branched $C_{1-10}$ fluoroalkyl group. For example, the $Y^2$ group may be a $C_{1-4}$ perfluoroalkyl group, which may be derived from the corresponding perfluorinated alkanesulfonic acid, such as trifluoromethanesulfonic acid or perfluorobutanesulfonic acid.

In an embodiment, the monomer of formula (VIII) may have the structure of formula (VIIIa) or (VIIIb):

(VIIIa)

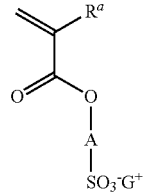

(VIIIb)

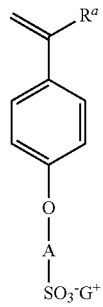

wherein A and $R^a$ are as defined for formula (VIII).

In formulae (VIII), (VIIIa), and (VIIIb), $G^+$ may have formula (IV):

wherein X, $R^c$, and z are the same as described in the embodiments above.

The polymerized product may further include a base-soluble monomer, a lactone-containing monomer, or a combination thereof. In an embodiment, the base-soluble monomer may be represented by formula (II) described above, and the lactone-containing monomer may be represented by formula (III) described above.

In an embodiment, the copolymer may include a polymerized product having any of the following structures:

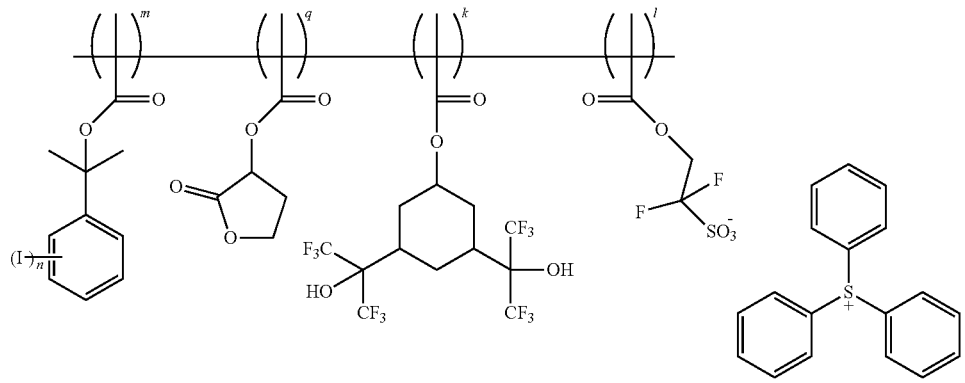

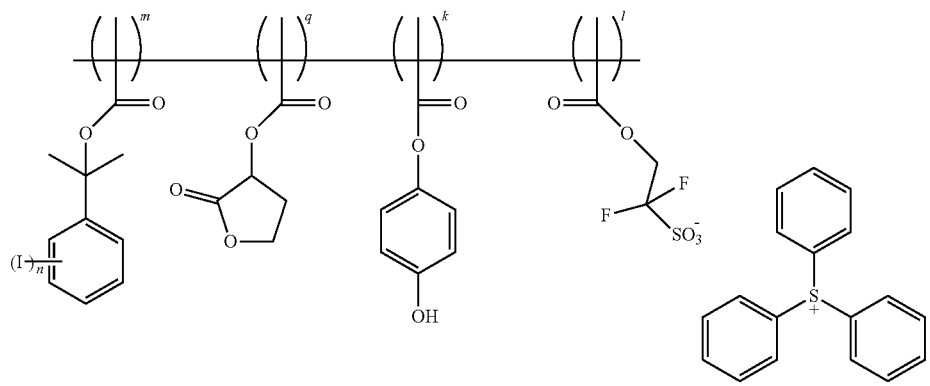

-continued
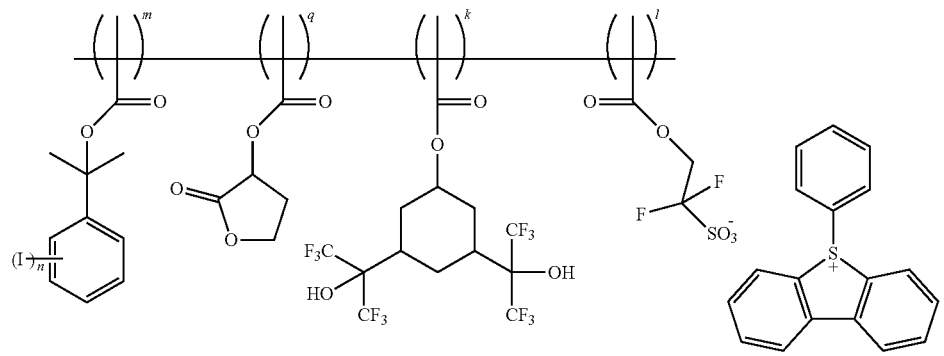
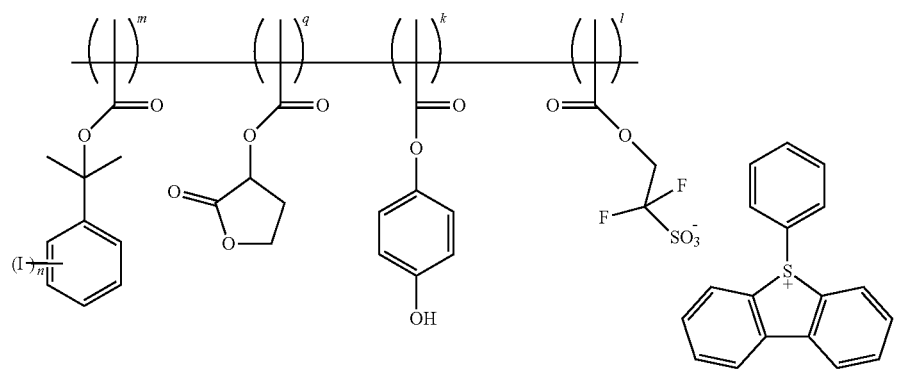
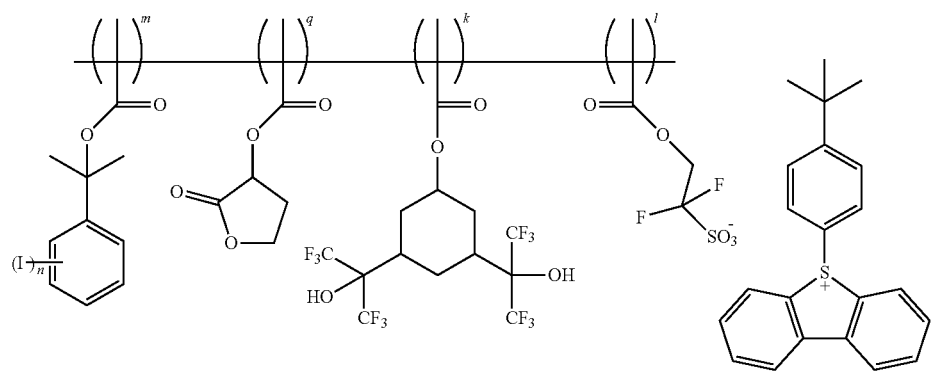
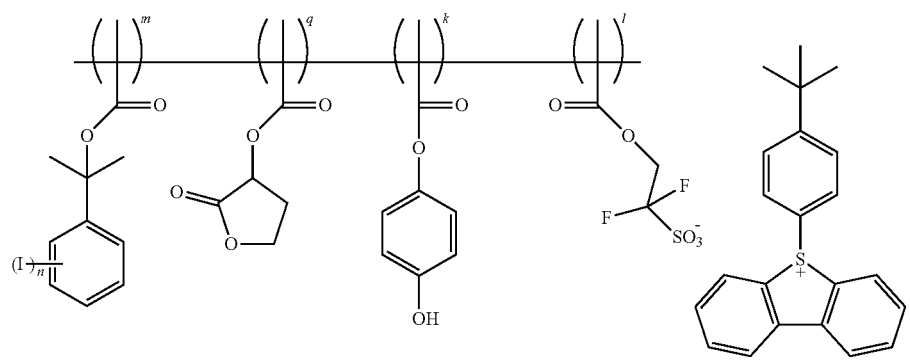

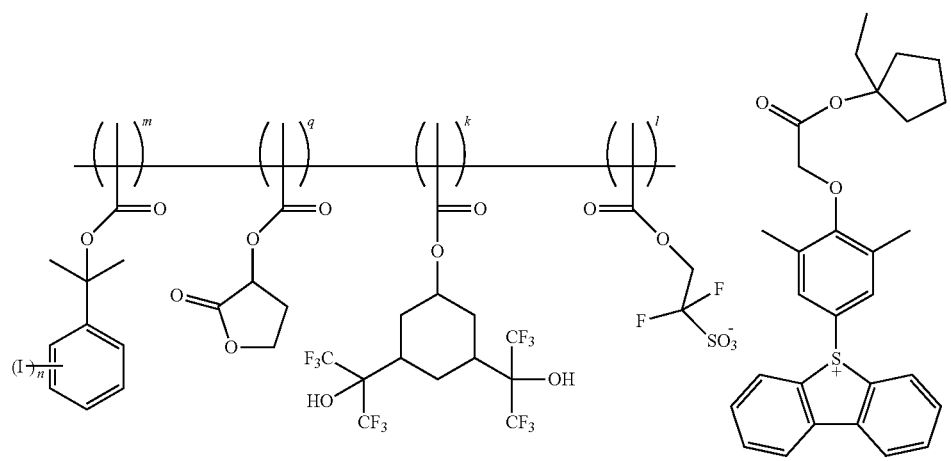

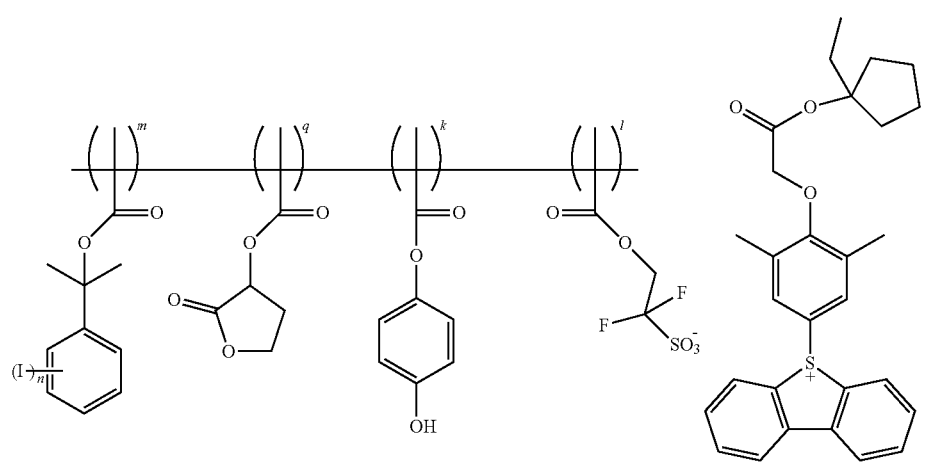

wherein k, l, m, and q represent mole fractions of the corresponding repeating units, and "I" is iodine and variable n is the same as described above.

Another embodiment provides a photoresist composition including the above copolymer and a coated substrate including: (a) a substrate having one or more layers to be patterned on a surface thereof; and (b) a layer of the above photoresist composition over the one or more layers to be patterned.

Yet another embodiment provides a method of forming an electronic device, including:

(a) applying a layer of the above photoresist composition on a surface of the substrate;

(b) pattern-wise exposing the photoresist composition layer to activating radiation; and (c) developing the exposed photoresist composition layer to provide a resist relief image.

Hereinafter, the present disclosure is illustrated in more detail with reference to examples. However, these examples are exemplary, and the present disclosure is not limited thereto.

Examples

The acronyms and chemical structures of monomers used in these examples are presented in Table 1. The synthesis of the monomer designated ECPPDBT F2 is described in U.S. Patent Publication No. 2014/0080058 A1.

TABLE 1

| Monomer Acronym | Chemical Structure |
| --- | --- |
| ECPPDBT F2 | 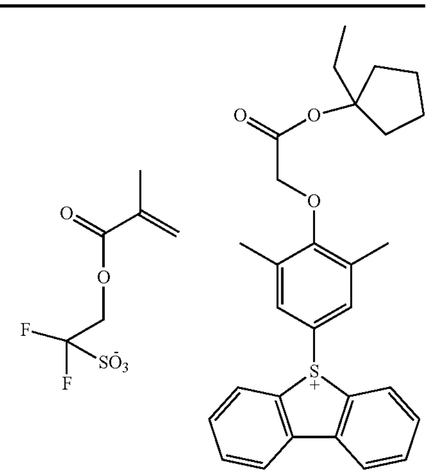 |

TABLE 1-continued

| Monomer Acronym | Chemical Structure |
|---|---|
| PPMA | (structure shown) |
| α-GBLMA | (structure shown) |
| DiHFA | (structure shown) |

Monomer Synthesis

Synthesis of two monomers are described. Grignard reagent solutions used herein were purchased from Aldrich and used as received. The synthetic scheme for the monomer designated 4-IPBMA is summarized in Figure 1. Under nitrogen atmosphere, an oven dry flask was charged with 100 mL of THF and 100 mL of 0.3 M ethylmagnesium bromide solution in THF. The Grignard solution was cooled to 0° C. and a solution of 4-iodobenzophenone (1, 50.0 g, 0.2 mol) in 200 mL THF was added dropwise under nitrogen atmosphere. The reaction mixture was warmed up to room temperature and stirring was continued for 4 h. An aqueous solution of ammonium chloride (100 mL, 1 M) was added to the reaction mixture. The resulting mixture was extracted twice with 100 mL of methylene chloride. The combined organic phase from the extractions was concentrated under reduced pressure to produce an oily crude product 2-(4-iodophenyl)butan-2-ol (2), which was used in the next step without further purification. Yield: 61 g.

In the next step, a solution of methacrolyl chloride (6.20 g, 59.3 mol) in 100 mL of methylene chloride was added dropwise to a solution made of 2-(4-iodophenyl)butan-2-ol (15.0 g, 54.2 mol) and triethylamine (6.2 g, 61.3 mol) in 100 mL of methylene chloride at 0° C. After the addition was completed, the mixture was allowed to warm up to room temperature and stirred for 16 h. Thin Layer Chromatography (TLC) test showed incomplete conversion. Additional 0.3 equivalents of methacrolyl chloride and 0.3 equivalents of triethylamine were added, and the mixture was stirred for an additional 12 h. The reaction mixture was washed with water (3×150 mL) and the organic phase was concentrated. The resulting residue was dissolved in 10 mL methylene chloride and passed through a short plug of silica-gel initially using heptane as an eluent followed by methylene chloride to collect fractions containing the product. To the combined fractions of the pure product was added 100 mg of the inhibitor dibutylhydroxytoluene (BHT), and the solvent was fully removed under reduced pressure to produce 10.5 g of the monomer 4-IPBMA (3) and the product was dried. Yield: 10.5 g.

$^1$H NMR (CDCl$_3$), δ: 7.75 (d, 2H, ArH), 7.25 (d, 2H, ArH), 6.20 (s, 1H, CH=CH), 5.70 (s, 1H, CH=CH), 2.01 (s, 3H, CH$_3$), 1.84-1.54 (m, 5H, CH$_3$CH$_2$), 0.8 (t, 3H, CH$_3$).

FIG. 1

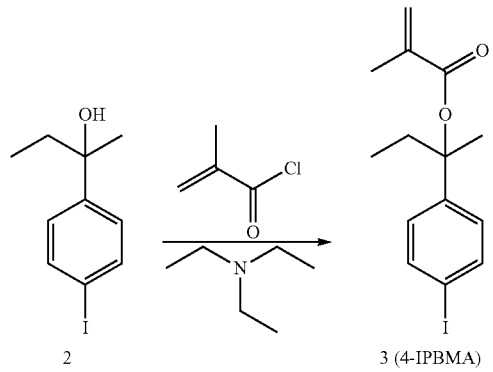

The synthetic scheme for the monomer designated 3-IP-PMA is summarized in Figure 2.

To a solution of methyl 3-iodobenzoate (4, 30 g, 0.122 mol) in 250 mL dry THF at 0° C. and under nitrogen atmosphere was slowly added 100 mL of 0.3 M solution of methylmagnesium bromide in ether. After the addition of the Grignard reagent was completed, the mixture was slowly warmed up to room temperature and stirring continued for an additional 3 h. Then, an aqueous solution of ammonium chloride (50 mL, 0.5 M) was added to the reaction mixture. The organic solvent was removed by distillation and the product was extracted with 150 mL methylene chloride. The methylene chloride solution was washed twice with 100 mL of water. The solvent from the organic phase was completely removed by distillation to produce the product 2-(3-iodophenyl)propan-2-ol 5 as colorless oil, which was used in the next step without further purification. Yield: 32 g (95%).

In the next step, a reaction flask was charged with a solution of 2-(3-iodophenyl)propan-2-ol (5, 32 g. 0.115 mol) in 150 mL of methylene chloride. The solution was cooled to 0° C. Methacryloyl chloride (18.0 g, 0.17 mol) and triethylamine (20 g, 0.20 mol) were added to the reaction flask, and the mixture was stirred at room temperature for 16 h. The organic phase was washed with water (3×100 mL), and the solvent was completely removed under reduced pressure. The crude material was dissolved in 150 mL of methylene chloride and washed twice with 100 mL of 0.5 M aqueous solution of sodium carbonate. The organic phase was concentrated and passed through a short pad of basic aluminum oxide using methylene chloride/heptane as eluent. The solvent fractions that contain the product were collected and the solvents were completely removed under reduced pressure to produce the product as colorless oil. Yield: 34 g (90%).

$^1$H NMR (CDCl$_3$), δ: 7.80 (s, 1H, ArH), 7.65 (d, 1H, ArH), 7.46 (d, 1H, ArH), 7.18 (T, 1H, ArH), 6.12 (S, 1H, CH=CH), 5.65 (s, 1H, CH=CH), 2.10 (s, 3H, CH$_3$), 1.70 (s, 6H, 2CH$_3$).

FIG. 2

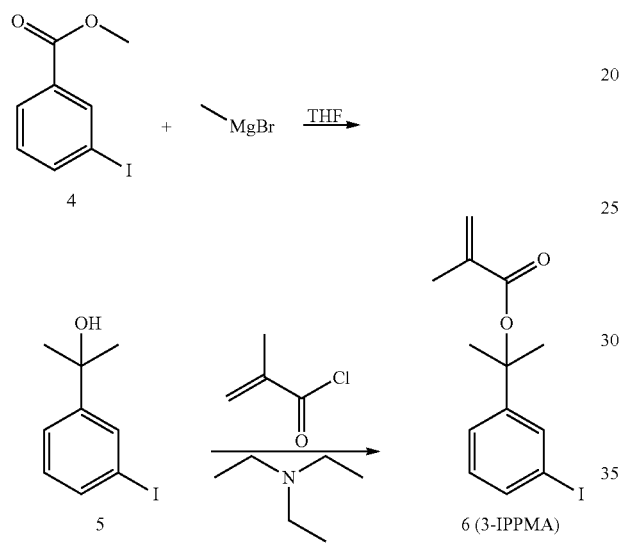

Copolymer Synthesis

This example describes the synthesis of three inventive and two comparative copolymers. Copolymer 1 was prepared from the monomers 4-IPBMA, α-GBLMA, DiHFA, at a molar feed ratio of 38.5/49.5/12. A feed solution was made by dissolving 4-IPBMA (7.97 g, 24.13 mmol), α-GBLMA (5.21 g, 31.0 mmol) and DiHFA (3.32 g, 7.0 mmol in 45.92 g of propylene glycole monomethyl ether acetate ("PG-MEA"). An initiator solution was prepared by dissolving 1.68 g of the azo initiator dimethyl 2,2'-azobis(2-methyl-propionate) (obtained as V-601 from Wako Pure Chemical Industries, Ltd.) in 10.8 g of PGMEA.

The polymerization was carried out in a 3-neck round bottom flask fitted with a water condenser and a thermometer to monitor the reaction in the flask. The reactor was charged with 4-IPBMA (0.46 g, 1.40 mmol), α-GBLMA (0.38 g, 2.23 mmol), DiHFA (0.67 g, 1.33 mmol) and in 17.52 g of propylene glycole monomethyl ether acetate ("PGMEA"), and the contents were heated to 75° C. The feed solution and the initiator solution were fed into the reactor using syringe pumps over a 4 h time period. The contents were then stirred for an additional 2 h. The contents were cooled to room temperature, diluted with tetrahydrofuran ("THF") to 25 weight percent, and precipitated into 10-fold (by weight) of a 7:3 (w/w) mixture of heptane and iso-propanol. The resulting copolymer 1 was isolated by filtration and dried under vacuum at 50° C. for 24 h.

The polymers set forth in Table 2 were prepared using the similar procedure used to make copolymer 1, except using the monomer types and molar feed ratios as specified in Table 2.

TABLE 2

| Co-polymer | Unit 1 (mole %) | Unit 2 (mole %) | Unit 3 (mole %) | Unit 4 (mole %) |
|---|---|---|---|---|
| 1 | 4-IPBMA (38.5) | α-GBLMA (49.5) | DiHFA (12.0) | |
| 2 | 3-IPPMA (38.5) | α-GBLMA (49.5) | DiHFA (12) | |
| 3 | 3-IPPMA (38.0) | α-GBLMA (46.0) | DiHFA (11) | ECPPDBT F2 (5.0) |
| 4 (comparative) | PPMA (38.5) | α-GBLMA (49.5) | DiHFA (12) | |
| 5 (comparative) | PPMA (38.0) | α-GBLMA (46.0) | DiHFA (11) | ECPPDBT F2 (5.0) |

Photoresist Preparation and Processing

Photoresist compositions containing copolymers 1 to 3 were each independently formulated as summarized in Table 3. Component amounts in Table 3 are based on total solids, excluding solvents. The non-polymeric photoacid generator was ECPPDBT AdOH-TFBS, which has the chemical structure:

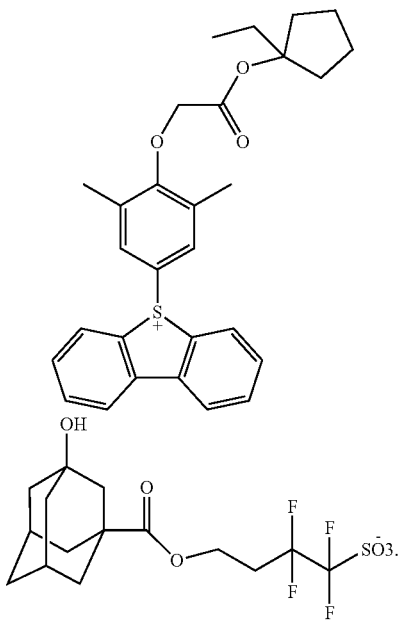

The quencher was trioctylamine (TOA). The surfactant was a fluorinated surfactant obtained as POLYFOX™ PF-656.

Compositions of two inventive and one comparative photoresist compositions are summarized in Table 3, where component amounts are expressed as weight percent based on total solids, excluding solvents.

TABLE 3

| Photoresist | Copolymer | PAG | Quencher | Surfactant |
|---|---|---|---|---|
| 1 | 65.31% Copolymer 1 | 32.0% ECPPDBT AdOH-TFBS | 4% | 0.1% |
| 2 | 65.31% Copolymer 2 | 32.0% ECPPDBT AdOH-TFBS | 4% | 0.1% |

TABLE 3-continued

| Photoresist | Copolymer | PAG | Quencher | Surfactant |
|---|---|---|---|---|
| 3 | 65.31% Copolymer 3 | 32.0% ECPPDBT AdOH-TFBS | 4% | 0.1 |
| 4 (comparative) | 65.31% Copolymer 4 | 32.0% ECPPDBT AdOH-TFBS | 4% | 0.1 |
| 5 (comparative) | 65.31% Copolymer 4 | 32.0% ECPPDBT AdOH-TFBS | 4% | 0.1% |

All formulations in Table 3 used a propylene glycol monomethyl ether acetate as a solvent. The resists were processed at a soft bake of 110° C. for 90 seconds and a post-exposure base at 100° C. for 60 seconds. Contrast curves at 248 nanometers were generated by coating the resist on a thick organic antireflective layer. The resist was exposed at 248 nanometers on a Canon TELACT tool. After a post-exposure bake, the resists were developed for 60 seconds using 0.26 N tetramethylammonium hydroxide solution. Film thickness values were measured using KLA Tencore OPTIPROBE™ 7341 thermal wave tool. Results from this evaluation are presented in Table 4, where "248 nm $E_0$" is the 248 nanometer exposure dose to clear, expressed in millijoules/centimeter$^2$.

Contrast Curve Measurement

Contrast curve measurements with EUV exposure source (13.5 nm) were obtained using a LithoTech Japan EUVES-9000 flood exposure tool. The resist was spin coated onto either an organic underlayer or a silicon wafer and baked at 110° C. for 90 seconds to form a 40-50 nm thick photoresist film. The resist was exposed to an increasing dose of 13.5 nm radiation in a step-wise manner, post-exposure baked at 100° C. for 60 seconds, and developed with 0.26 N aqueous tetramethylammonium hydroxide solution for 60 seconds to form a relief image pattern of exposed and non-exposed areas. Thickness was measured at each exposed area using a KLA Thermawave-7 ellipsometer and plotted vs. dose. Dose-to-clear values ($E_0$) were calculated at 10% or less remaining film thickness. As can be seen, photoresists 1 and 2 which contain terpolymer with 4-IPBMA or 3-IPPMA acid cleavable repeat units have higher photospeed under EUV exposure compared to the comparative photoresist 4 which includes terpolymer with "iodo-free" PPMA acid cleavable repeat units. Photoresist 3 which contains polymer-bound PAG that includes 3-IPPMA has a higher photospeed under EUV exposure compared to the comparative photoresist 5 which includes polymer-bound PAG that includes "iodo free" PPMA acid cleavable repeat units.

TABLE 4

| Photoresist | 248 nm $E_0$ (mJ/cm$^2$) | EUV $E_0$ (mJ/cm$^2$) |
|---|---|---|
| 1 | 9.2 | 1.7 |
| 2 | 9.4 | 1.6 |
| 3 | 8.4 | 1.6 |
| 4 (comparative) | 7.2 | 2.1 |
| 5 (comparative) | 4.8 | 2.1 |

While this disclosure has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

The invention claimed is:

1. A monomer having formula (I):

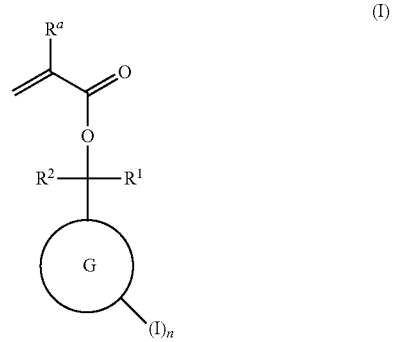

wherein in formula (I):
$R^a$ is H, F, —CN, $C_{1-10}$ alkyl group, or $C_{1-10}$ fluoroalkyl group;
$R^1$ and $R^2$ are different and each chosen from an unsubstituted or substituted $C_{1-10}$ linear or branched alkyl group, an unsubstituted or substituted $C_{3-10}$ cycloalkyl group, an unsubstituted or substituted $C_{3-10}$ alkenylalkyl group, an unsubstituted or substituted $C_{3-10}$ alkynylalkyl group, or an unsubstituted or substituted $C_{6-30}$ aryl group, wherein $R^1$ and $R^2$ optionally comprise at least one linking group selected from O and S, and wherein $R^1$ and $R^2$ together optionally form a ring;

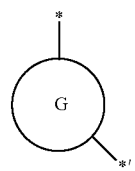

represents a monocyclic or polycyclic unsubstituted or substituted $C_{6-30}$ arylene group or a monocyclic or polycyclic unsubstituted or substituted $C_{3-30}$ heteroarylene group, wherein "*" and "*'" indicate a point of attachment to a neighboring group or atom;
"I" represents iodine; and
n is 1, 2, 3, 4, 5, 6, 7, 8, and 9.

2. The monomer of claim 1, wherein the $C_{6-30}$ arylene group is a monocyclic $C_{6-30}$ arylene group, a fused bicyclic $C_{6-30}$ arylene group, or a singly bonded $C_{6-30}$ arylene group.

3. The monomer of claim 1, wherein $R^1$ and $R^2$ are different and each chosen from an unsubstituted $C_{1-10}$ linear or branched alkyl group.

4. The monomer of claim 3, wherein one of $R^1$ and $R^2$ is an unsubstituted $C_{1-10}$ linear or branched alkyl group and the other one of $R^1$ and $R^2$ is a $C_{1-10}$ linear or branched alkyl group substituted with at least one fluorine atom.

5. The monomer of claim 1, wherein n is 1, 2, or 3.

6. The monomer of claim 1, wherein one of $R^1$ and $R^2$ is an unsubstituted or substituted $C_{1-10}$ linear or branched alkyl group and the other one of $R^1$ and $R^2$ is an unsubstituted or substituted $C_{3-10}$ branched alkyl group, a $C_{2-10}$ linear or branched alkyl group substituted with at least one fluorine atom, an unsubstituted or substituted $C_{3-10}$ cycloalkyl group, an unsubstituted or substituted $C_{3-10}$ alkenylalkyl group, an unsubstituted or substituted $C_{3-10}$ alkynylalkyl group, or an unsubstituted or substituted $C_{6-30}$ aryl group, wherein $R^1$ and $R^2$ optionally comprise at least one linking group selected from O and S, and wherein $R^1$ and $R^2$ together optionally form a ring.

7. The monomer of claim 1, wherein one of $R^1$ and $R^2$ is an unsubstituted $C_{1-10}$ linear alkyl group and the other one of $R^1$ and $R^2$ is an unsubstituted $C_{3-10}$ branched alkyl group.

8. A copolymer comprising a polymerized product of a monomer of claim 1.

9. The copolymer of claim 8, further comprising a polymerized product of a base-soluble monomer, a lactone-containing monomer, or a combination thereof.

10. The copolymer of claim 9, wherein the base-soluble monomer is represented by formula (II), and wherein the lactone-containing monomer is represented by formula (III):

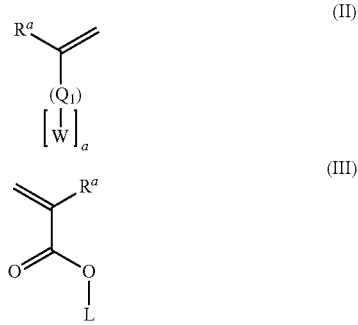

wherein
each $R^a$ is independently H, F, $C_{1-10}$ alkyl, or $C_{1-10}$ fluoroalkyl;
$Q_1$ is an ester-containing or non-ester containing group selected from $C_{1-20}$ alkyl, $C_{3-20}$ cycloalkyl, $C_{6-20}$ aryl, and $C_{7-20}$ aralkyl;
W is a base-reactive group comprising —C(=O)—OH; —C(CF$_3$)$_2$OH; —NH—SO$_2$—Y$^1$ where Y$^1$ is F or $C_{1-4}$ perfluoroalkyl; an aromatic —OH; or an adduct of any of the foregoing with a vinyl ether;
a is an integer of 1 to 3; and
L is a monocyclic, polycyclic, or fused polycyclic $C_{4-20}$ lactone-containing group.

11. The copolymer of claim 8, further comprising a polymerized product of a monomer comprising a photoacid generator.

12. The copolymer of claim 11, wherein the photoacid generator monomer comprising a polymerizable group is represented by formula (VIII):

wherein
$R^a$ is independently H, F, $C_{1-10}$ alkyl, or $C_{1-10}$ fluoroalkyl;
$Q_2$ is a single bond or an ester-containing or non-ester containing, fluorinated or non-fluorinated group selected from $C_{1-20}$ alkylene, $C_{3-20}$ cycloalkylene, $C_{6-20}$ arylene, and $C_{7-20}$ aralkylene group;

A is an ester-containing or non ester-containing, fluorinated or non-fluorinated group selected from $C_{1-20}$ alkylene, $C_{3-20}$ cycloalkylene, $C_{6-20}$ arylene, and $C_{7-20}$ aralkylene;
Z is an anionic moiety comprising sulfonate, an anion of a sulfonamide, or an anion of a sulfonimide; and
G$^+$ has formula (IV):

wherein
X is S or I,
each $R^c$ is unsubstituted or substituted, halogenated or non-halogenated and is independently $C_{1-30}$ alkyl; a polycyclic or monocyclic $C_{3-30}$ cycloalkyl; a polycyclic or monocyclic $C_{4-30}$ aryl, wherein when X is S, one of the $R^c$ is optionally attached to one adjacent $R^c$ by a single bond, and
z is 2 or 3, wherein when X is I, z is 2, or when X is S, z is 3.

13. A photoresist composition comprising:
a copolymer of claim 8;
a photoacid generator; and
a solvent.

14. The photoresist composition of claim 13, wherein the photoacid generator has formula G$^+$A$^-$,
wherein G$^+$ has formula (IV):

wherein
X is S or I,
each $R^c$ is unsubstituted or substituted, halogenated or non-halogenated, and is independently $C_{1-30}$ alkyl; a polycyclic or monocyclic $C_{3-30}$ cycloalkyl; a polycyclic or monocyclic $C_{4-30}$ aryl, wherein when X is S, one of the $R^c$ is optionally attached to one adjacent $R^c$ by a single bond, and
z is 2 or 3, wherein when X is I, z is 2, or when X is S, z is 3; and
wherein A$^-$ is a non-polymerizable organic anion.

15. The photoresist composition of claim 14, wherein G$^+$ has formula (V), (VI), or (VII):

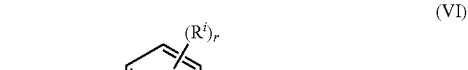

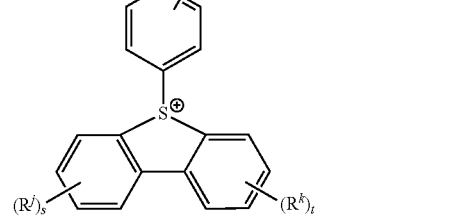

-continued

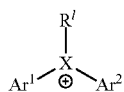
(VII)

wherein
X is I or S,
$R^h$, $R^i$, $R^j$, and $R^k$ are unsubstituted or substituted and are each independently hydroxy, nitrile, halogen, $C_{1-30}$ alkyl, $C_{1-30}$ fluoroalkyl, $C_{3-30}$ cycloalkyl, $C_{1-30}$ fluorocycloalkyl, $C_{1-30}$ alkoxy, $C_{3-30}$ alkoxycarbonylalkyl, $C_{3-30}$ alkoxycarbonylalkoxy, $C_{3-30}$ cycloalkoxy, $C_{5-30}$ cycloalkoxycarbonylalkyl, $C_{5-30}$ cycloalkoxycarbonylalkoxy, $C_{1-30}$ fluoroalkoxy, $C_{3-30}$ fluoroalkoxycarbonylalkyl, $C_{3-30}$ fluoroalkoxycarbonylalkoxy, $C_{3-30}$ fluorocycloalkoxy, $C_{5-30}$ fluorocycloalkoxycarbonylalkyl, $C_{5-30}$ fluorocycloalkoxycarbonylalkoxy, $C_{6-30}$ aryl, $C_{6-30}$ fluoroaryl, $C_{6-30}$ aryloxy, $C_{6-30}$ fluoroaryloxy, or a $C_{2-30}$ acetal group comprising —O—C($R^{11}R^{12}$)—O— (wherein $R^{11}$ and $R^{12}$ are each independently hydrogen or a $C_{1-30}$ alkyl group), each of which is unsubstituted or substituted;
$Ar^1$ and $Ar^2$ are independently $C_{10-30}$ fused or singly bonded polycyclic aryl groups;
$R^1$ is a lone pair of electrons where X is I, or a $C_{6-20}$ aryl group where X is S; p is an integer of 2 or 3, wherein when X is I, p is 2, and where X is S, p is 3,
q and r are each independently an integer from 0 to 5, and s and t are each independently an integer from 0 to 4.

16. A coated substrate, comprising: (a) a substrate having one or more layers to be patterned on a surface thereof; and (b) a layer of a photoresist composition of claim 13 over the one or more layers to be patterned.

17. A method of forming an electronic device, comprising:
(a) applying a layer of the photoresist composition of claim 13 over a surface of the substrate;
(b) pattern-wise exposing the photoresist composition layer to activating radiation; and
(c) developing the exposed photoresist composition layer to provide a resist relief image.

18. A photoresist composition comprising:
a copolymer comprising a polymerized product of a monomer having formula (I):

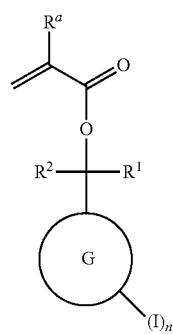
(I)

wherein in formula (I):
$R^a$ is H, F, —CN, $C_{1-10}$ alkyl group, or $C_{1-10}$ fluoroalkyl group;
$R^1$ and $R^2$ are each independently an unsubstituted or substituted $C_{1-10}$ linear or branched alkyl group, an unsubstituted or substituted $C_{3-10}$ cycloalkyl group, an unsubstituted or substituted $C_{3-10}$ alkenylalkyl group, an unsubstituted or substituted $C_{3-10}$ alkynylalkyl group, or an unsubstituted or substituted $C_{6-30}$ aryl group, wherein $R^1$ and $R^2$ optionally comprise at least one linking group selected from O and S, and wherein $R^1$ and $R^2$ together optionally form a ring;

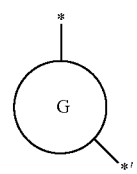

represents a monocyclic or polycyclic unsubstituted or substituted $C_{6-30}$ arylene group or a monocyclic or polycyclic unsubstituted or substituted $C_{3-30}$ heteroarylene group, wherein "*" and "*'" indicate a point of attachment to a neighboring group or atom;
"I" represents iodine; and
n is 1, 2, 3, 4, 5, 6, 7, 8, and 9;
a photoacid generator having formula $G^+A^-$, wherein $G^+$ has formula (VI):

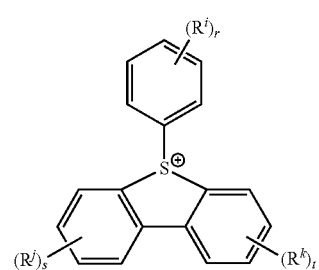
(VI)

and $A^-$ is a non-polymerizable organic anion;
and a solvent.

19. A coated substrate, comprising: (a) a substrate having one or more layers to be patterned on a surface thereof; and (b) a layer of a photoresist composition of claim 18 over the one or more layers to be patterned.

20. A method of forming an electronic device, comprising:
(a) applying a layer of the photoresist composition of claim 18 over a surface of the substrate;
(b) pattern-wise exposing the photoresist composition layer to activating radiation; and
(c) developing the exposed photoresist composition layer to provide a resist relief image.

* * * * *